United States Patent
Nathan et al.

(10) Patent No.: US 10,143,713 B2
(45) Date of Patent: Dec. 4, 2018

(54) IN OVO DELIVERY OF PROBIOTIC CULTURES

(71) Applicant: Biogaia AB, Stockholm (SE)

(72) Inventors: Uma Nathan, Cary, NC (US); Bo Möllstam, Lerum (SE)

(73) Assignee: Biogaia AB, Stockholm (SE)

( * ) Notice: Subject to any disclaimer, the term of this patent is extended or adjusted under 35 U.S.C. 154(b) by 0 days.

(21) Appl. No.: 15/108,047

(22) PCT Filed: Jun. 24, 2015

(86) PCT No.: PCT/EP2015/064310
§ 371 (c)(1),
(2) Date: Jun. 24, 2016

(87) PCT Pub. No.: WO2015/197728
PCT Pub. Date: Dec. 30, 2015

(65) Prior Publication Data
US 2017/0095516 A1   Apr. 6, 2017

Related U.S. Application Data

(60) Provisional application No. 62/016,285, filed on Jun. 24, 2014.

(51) Int. Cl.
| | | |
|---|---|---|
| *A61K 39/12* | (2006.01) | |
| *A23K 1/00* | (2006.01) | |
| *A61K 35/747* | (2015.01) | |
| *A01K 45/00* | (2006.01) | |
| *A23K 10/16* | (2016.01) | |
| *A23K 10/18* | (2016.01) | |
| *A23K 50/75* | (2016.01) | |
| *A61K 39/255* | (2006.01) | |
| *C12N 7/00* | (2006.01) | |
| *A61K 39/00* | (2006.01) | |

(52) U.S. Cl.
CPC .......... *A61K 35/747* (2013.01); *A01K 45/007* (2013.01); *A23K 10/16* (2016.05); *A23K 10/18* (2016.05); *A23K 50/75* (2016.05); *A61K 39/12* (2013.01); *A61K 39/255* (2013.01); *C12N 7/00* (2013.01); *A61K 2039/54* (2013.01); *A61K 2039/552* (2013.01); *C12N 2710/16334* (2013.01); *C12N 2760/18134* (2013.01)

(58) Field of Classification Search
None
See application file for complete search history.

(56) References Cited

U.S. PATENT DOCUMENTS

2007/0243212 A1   10/2007   Doelling et al.

FOREIGN PATENT DOCUMENTS

WO   WO 92/12638 A1   8/1992

OTHER PUBLICATIONS

International Preliminary Report on Patentability corresponding to International Patent Application No. PCT/EP2015/064310 (5 pages) (dated Sep. 22, 2016).
International Search Report and the Written Opinion of the International Searching Authority corresponding to International Patent Application No. PCT/EP2015/064310 (8 pages) (dated Sep. 8, 2015).
Wexler D. "Technically Speaking: Use of Vaccines with Diluents" (Nov. 2010) Handout from the Immunization Action Coalition printed from immunize.org website.
National Animal Health Emergency Management System (NAHEMS) Guidelines: Vaccination for Contagious Diseases (Jul. 2011) 58 pages.

*Primary Examiner* — Jennifer E Graser
(74) *Attorney, Agent, or Firm* — Myers Bigel, P.A.

(57) ABSTRACT

The present invention generally relates to a strain of *Lactobacillus* probiotic bacteria and a poultry vaccine for use in the in ovo vaccination of poultry, wherein said strain and said vaccine are administered to an embryonated poultry egg. Compositions suitable for use in an in ovo vaccination protocol for poultry comprising a strain of *Lactobacillus* probiotic bacteria and a vaccine diluent which is suitable for the poultry vaccine to be used in said vaccination protocol are also provided, as are suitable kits for use in the invention.

7 Claims, No Drawings

IN OVO DELIVERY OF PROBIOTIC CULTURES

STATEMENT OF PRIORITY

This application is a 35 USC § 371 national phase application of International Application Serial No. PCT/EP2015/064310, filed Jun. 24, 2015, which claims the benefit, under 35 U.S.C. § 119(e), of U.S. Provisional Application Ser. No. 62/016,285, filed Jun. 24, 2014 the entire contents of each of which are incorporated by reference herein.

FIELD OF THE INVENTION

The present invention generally relates to a method for delivering viable microbial cells in the form of probiotic bacteria, also called "direct feed microorganisms," or probiotics, to poultry in ovo. The invention also relates to compatible compositions suitable for delivery along with vaccine products.

BACKGROUND OF THE INVENTION

A number of documents have appeared in the literature describing the scientific basis for use of probiotics, or DFM's (direct feed microorganisms), as intestinal inoculants for production animals. Since Metchnikoff's early reports, several studies have shown the ability of lactobacilli, for example, to suppress coliform growth. Feeding viable *Lactobacillus acidophilus* cells to young dairy calves was shown to reduce the incidence of diarrhea, and increase the numbers of lactobacilli and reduce coliform counts in feces.

Probiotics for animals are bacterial or yeast preparations that are administered orally or added to feeds. The most commonly used animal probiotics are strains of the lactic acid bacteria (LAB) species, particularly those classified in the following genera: *Lactobacillus, Lactococcus* and *Enterococcus*. Included among these are the following species: *Lactobacillus acidophilus, Lactobacillus bulqaricus, Lactobacillus plantarum, Lactobacillus casei, Lactobacillus lactis, Lactococcus lactis, Lactococcus thermophilus, Lactococcus diacetylactis* and *Enterococcus faecium*. Besides these LAB, some species of *Bacillus* (*Bacillus subtilis, Bacillus toyoi*) and yeasts and molds (*Saccharomyces cerevisiae, Aspergillus oryzae,* and *Torulopsis* sp.) are used.

It is generally held that during periods of low disease resistance, such as stress, undesirable microorganisms are able to proliferate in the GI tract of animals, humans included. Maintaining a normal, healthy balance of microorganisms is deemed to be critical during for example such stressful periods. The concept underlying use of probiotics therefore is that if sufficient numbers of an appropriate microorganism(s) are introduced into the intestinal tract (i) at times of stress and/or disease, (ii) at birth, or (iii) after antibiotic treatment (when minimal LAB are present), the negative consequences of the microbial imbalances can be minimized or overcome. Using such preparations of live, naturally occurring microorganisms helps restore and maintain the proper balance of beneficial microbes in the GI tract during times of stress, disease, and following antibiotic therapy. Some of the major problems or limitations encountered in commercial scale application of probiotics to animals are (i) the use of correct and documented probiotic strain for the purpose, and (ii) the availability of suitable delivery systems, and (iii) the ability to get the probiotic preparations to the animals as quickly as possible after birth. This is particularly true in animal production when pelletized feeds are used, as is the case in the poultry industry. The pelletization process generally includes one or more heating steps involving temperatures high enough to pasteurize or sterilize the feed components, thereby precluding incorporation of viable microorganisms into these feeds prior to pelletization.

The invention herein solves those problems with the undesired microorganisms as described below.

SUMMARY OF THE INVENTION

The present invention herein aims to provide a delivery of suitable probiotic bacteria to poultry in ovo for high hatchability and low mortality of the chickens.

An object of the present invention is to provide a composition comprising certain strains of lactic acid bacteria and together with a vaccine diluent to poultry in ovo. Using the same diluent as for the vaccines used, increases the compatibility and reduces the risk for negative interference between the probiotic bacteria and the vaccine. This enables an effective way of delivery of the probiotic bacteria as it can be done without reducing the effect of a used vaccine or the used probiotic bacteria.

Another object of the present invention is to provide a composition comprising certain strains of *Lactobacillus reuteri* and suitable vaccine diluent. More specifically the invention is to provide a composition comprising *Lactobacillus reuteri* strain T-1, ATCC 55149 (isolated from turkey) and strain 11284 ATCC 55148 (isolated from chicken) and suitable vaccine diluent for the presently used vaccine.

DETAILED DESCRIPTION OF THE INVENTION AND PREFERRED EMBODIMENTS THEREOF

The present invention describes novel methods and processes for delivering viable probiotics in ovo. The probiotic used to develop these methods is *Lactobacillus reuteri*. This species was chosen because it has demonstrated good and reliable efficacy as a DFM in poultry.

*Lactobacillus reuteri* is a species of lactic acid bacteria recognized since the turn of the century. Originally assigned different species names (e.g., *Lactobacillus fermentum* biotype II), it obtained distinct species status in 1980 and is registered in the 1988 edition of Bergey's manual. It is found in foods, particularly dairy products and meats, but exists primarily in the GI tract of healthy animals, including humans.

Poultry production is an important source of animal protein for lots of people around the world. Poultry products include eggs, chickens, and turkeys. Different types of poultry are suitable for specific purposes such as layers are used for egg production whereas broilers have been developed and bred for optimal and fast growth. Modern poultry production many times takes place in enclosed buildings to protect the birds from weather, predators, but also to minimize the risk of diseases spread from wild birds. In broiler production it is important to ensure a disease free environment and to find suitable methods of preparing the broilers for a healthy life. As an example, enterobacterial human pathogens, such as *Salmonella* spp. could contaminate poultry meat and eggs. The bacteria colonize the intestinal tract but it does not normally cause disease in the poultry but an infection could be devastating to human. There have been efforts to reduce this problem and focus has been put on sanitary actions during production and processing of the meat and egg, but such methods are time-consuming, expensive and do not guarantee total eradication of the bacteria and this still remains a problem.

Another attempt to combat these enterobacterial pathogens is to vaccinate the poultry to protect them from disease. Another way is to use suitable probiotics such as *Lactobacillus reuteri*, especially strains ATCC55148 and 55149 to reduce the number of pathogens.

Vaccination aims to mimic the development of naturally acquired immunity by inoculation of non-pathogenic but still immunogenic components of the pathogen in question. The criteria for successful animal and veterinary vaccines can be very different to those for human and aims for example at improving production, reducing or eliminating the risk for consumers in acquiring food-borne infections. The veterinary vaccine market is growing due to new available technologies and also the restricted use of antibiotics. In addition to *Salmonella*, two other common diseases in poultry, which can be vaccinated against, are Marek's disease virus (MDV) and Newcastle disease virus. Marek's disease is a highly contagious viral disease primarily in chickens. It is caused by a herpersvirus and characterized by the presence of T cell lymphoma as well as infiltration of nerves and organs by lymphocytes. Viruses related to MDV can be used as vaccine strains, for example Herpesvirus of Turkeys (HVT), which causes no apparent disease in turkeys. Newcastle disease virus is a paramyxovirus. The virus can also penetrate eggshells and thereby infecting the embryo. There are many Newcastle disease vaccines suitable for use in commercial chickens.

A vaccine can be prepared in different ways, one example is to grow the vaccine strain and then use as is or form into a vaccine composition by combining the growing culture with a suitable diluent. A diluent should not effect the stability and vitality of the vaccine culture in a negative way. The diluent is preferably free of chlorine, antibiotics, antimicrobials, or any other agent that may be harmful to the live vaccine organisms.

There are different forms of vaccine administration, and one technique that is frequently used is in ovo injection. In ovo vaccination was introduced in the US for over 20 years ago and is a very effective technology in order to obtain early immunity. It is also an effective way of mass vaccination, making it an appropriate method for use in poultry production such as broiler production. It enables individual injection of each egg, which means that every bird is vaccinated.

The present invention generally provides a means for delivering lactobacilli and other DFM's into eggs of avian species, so that these microorganisms may be well established in the bird gastrointestinal system at hatching time.

An object of the invention is to provide a delivery of especially suitable probiotic bacteria to poultry in ovo for high hatchability and low mortality of the chickens. This is done through the use of lactic acid bacteria, preferably of the *Lactobacillus reuteri* species and preferably isolated from poultry.

A further object of the present invention is to provide cultures of *Lactobacillus reuteri* injected into eggs by puncturing the egg aseptically above the air cell with a needle.

Another object of the present invention is to provide cultures of *Lactobacillus reuteri* injected into the amniotic fluid of eggs by puncturing the egg aseptically with a needle.

An object of the present invention is to provide a composition comprising certain strains of lactic acid bacteria and together with a vaccine diluent to poultry in ovo. Using the same diluent as for the vaccines used, increases the compatibility and reduces the negative interference by the probiotic bacteria and the vaccine. This enables an effective way of delivery of the probiotic bacteria as it can be done without reducing the effect of a used vaccine or the used probiotic bacteria.

Another object of the present invention is to provide a composition comprising certain strains of *Lactobacillus reuteri* and suitable vaccine diluent. More specifically the invention is to provide a composition comprising *Lactobacillus reuteri* strain T-1, ATCC 55149 (isolated from turkey) and strain 11284 ATCC 55148 (isolated from chicken) and suitable vaccine diluent for the presently used vaccine, preferably for Marek's vaccine, for example from Merial Inc.

The present invention is thus based on the provision of conditions which allow for the compatibility of a probiotic bacteria and a poultry vaccine. The inventors have found that this can be done through the use of the same diluent for the probiotic as is suitable for the poultry vaccine. The ability to use the same diluent for the probiotic as for the vaccine increases the compatibility and reduces the negative interference between the probiotic bacteria and the vaccine so that the probiotic can still function effectively as a probiotic and the vaccine can still function effectively as a vaccine.

It is well known and recognised in the art that vaccines require suitable and specific diluents and that in most cases diluents are not interchangeable. Vaccine diluents are liquids which are generally provided separately from the vaccine and are used to dilute a vaccine to the proper concentration prior to administration. For example, a diluent can be used to reconstitute a lyophilised or freeze dried vaccine or simply to dilute a vaccine which is already in liquid form. However, diluents are not just for dissolving vaccines or diluting vaccines; they are designed to meet an individual vaccine's specific requirements, for example in terms of volume, sterility, pH and chemical balance. Vaccines are thus generally very sensitive to the diluent they are exposed to, and an incorrect diluent can result in an adverse effect on the functionality of a vaccine or the vaccine not working effectively. For this reason, in most cases, diluents are not interchangeable and are specific for the vaccine concerned. If the wrong diluent is used, the vaccination will always need to be repeated.

Surprisingly given the above sensitivities, the present inventors found that probiotic bacteria that can have beneficial effects in poultry could be diluted in the same diluent as a poultry vaccine and combined with a poultry vaccine without significantly interfering with the activity of the vaccine. Using the same diluent for the probiotic as for the vaccine increases the compatibility and reduces the negative interference between the probiotic bacteria and the vaccine. This enables an effective way of delivering the probiotic bacteria (and the vaccine) as it can be done whilst maintaining a beneficial effect of a vaccine and a beneficial effect of the probiotic bacteria which are used. In this way combination therapies can be provided in which vaccines and probiotics are administered. In particular, the inventors have shown that *Lactobacillus reuteri* strains can be diluted in a vaccine diluent developed for Marek's disease and can be mixed with a live vaccine for Marek's disease made up with the same diluent, without eliminating the ability of the vaccine to replicate. In other words, the activity of the vaccine was maintained to a useful extent in the presence of the probiotic.

In addition, the inventors have shown that the probiotic strains when diluted in a vaccine diluent and administered to poultry in ovo have beneficial effects on the poultry. In other words, the probiotic activity of the strains was maintained to a useful extent in the presence of the vaccine diluent.

Thus, one aspect of the invention provides a composition suitable for use in an in ovo vaccination protocol for poultry comprising a strain of *Lactobacillus* probiotic bacteria and a vaccine diluent which is suitable for the poultry vaccine to be used in said vaccination protocol.

Viewed alternatively, the present invention provides a composition comprising a strain of *Lactobacillus* probiotic bacteria and a vaccine diluent suitable for an in ovo poultry vaccine.

The term "probiotic bacteria" as used herein refers to live microorganisms which when administered in adequate amounts confer a health benefit on the host, in this case a type of poultry.

Poultry can benefit from probiotic bacteria through a plethora of ways. For example, the presence of the probiotic bacteria in the GI tract of poultry can prevent or inhibit the proliferation of pathogens, suppress production of virulence factors by pathogens, or modulate the immune response in a pro-inflammatory or an anti-inflammatory way.

A primary aim of the present invention is to prepare a poultry embryo for a life outside the egg once hatched, for example to provide the poultry with useful probiotic bacteria which will for example prevent or reduce conditions associated with non-optimal intestinal flora or enterobacterial pathogens in the poultry, or improve poultry hatchability or reduce poultry mortality, together with the provision of poultry vaccines which will prevent or reduce certain diseases which have a detrimental effect on poultry. Conveniently such probiotic bacteria and poultry vaccines are administered in ovo which then allows these agents to pass to the gastrointestinal tract of the poultry and thereby exert their positive effects on the poultry by the appropriate mechanism.

Although preferred probiotic bacteria for use in the present invention are strains of *Lactobacillus* bacteria, and, more specifically, *Lactobacillus reuteri* bacteria, any appropriate probiotic bacteria can be used in the compositions, methods and uses, etc., of the present invention providing that said bacteria is capable of colonising the gastrointestinal tract of the poultry being vaccinated and providing that its ability to function as a probiotic and provide a health benefit in the poultry is retained to a useful extent.

Thus, other appropriate probiotics for use in the present invention are strains of the lactic acid bacteria (LAB) species, for example those classified in the following genera: *Lactobacillus*, *Lactococcus* and *Enterococcus*. Included among these are the following species: *Lactobacillus acidophilus*, *Lactobacillus bulqaricus*, *Lactobacillus plantarum*, *Lactobacillus casei*, *Lactobacillus lactis*, *Lactococcus lactis*, *Lactococcus thermophilus*, *Lactococcus diacetylactis* and *Enterococcus faecium*.

It is generally preferred that known strains and pure cultures of probiotic bacteria are used in the present invention, rather than unknown mixtures and preparations of probiotic bacteria. More than one type of strain, or mixtures of known or pure strains of probiotic bacteria can however be used in the present invention. Indeed, such mixtures are preferred in some embodiments. Such mixtures or combinations of probiotic bacteria can be administered together in a single composition or administered separately.

When the vaccine (and corresponding diluent) used in the invention is a vaccine (and diluent) suitable for Marek's disease (for example a commercially produced Marek's disease virus vaccine and its diluent), in particular a vaccine which comprises a strain of turkey herpes virus or a strain of chicken herpes virus, or a combination thereof, then preferred probiotic bacteria for use are *L. reuteri* strain T1 (ATCC 55149) or *L. reuteri* strain 11284 (ATCC 55148), or mixtures thereof. However, it is envisaged that other strains of *L. reuteri* (and indeed other genera of probiotic bacteria) can be selected which are compatible with these and indeed other vaccines and diluents. Indeed, other strains of *L. reuteri* or other types of *Lactobacillus* probiotic bacteria can be selected for compatibility with particular poultry vaccines and their diluents.

Thus, in general, preferred *L. reuteri* strains for use in the present invention are *L. reuteri* strain T1 (ATCC 55149) or *L. reuteri* strain 11284 (ATCC 55148), or mixtures thereof which can be administered together or separately. The *Lactobacillus reuteri* strain T1 (ATCC 55149) and the *L. reuteri* strain 11284 (ATCC 55148) were deposited at the American Type Culture Collection (12301 Parklawn Drive, Rockville, Md. 20852, USA) on 29 Jan. 1991.

In embodiments where more than one strain of probiotic bacteria is used in a mixture in a single composition, or where more than one strain of probiotic bacteria is used but they are administered separately, then any appropriate ratio of the bacteria can be used providing that the probiotic function of the strains is retained to a useful extent. Such ratios can readily be determined by a person skilled in the art. For example, such a combination of two strains might be used at a ratio of 1:10, 1:5, 1:1, 5:1, or 10:1.

Appropriate vaccines (and diluents) for use in the present invention are any poultry vaccines which are suitable for in ovo administration. Because of the necessary regulations concerning poultry vaccines such vaccines for use in the present invention will generally have been approved by the necessary Regulatory Authorities (for example will be USDA approved) for veterinary use/poultry use and will generally be supplied commercially together with an appropriate vaccine diluent which has been selected or developed for that vaccine. There are many vaccines available for poultry which can be used to vaccinate against many different diseases, and any of these, or a combination of these, may be used in the present invention. As mentioned elsewhere herein, preferred vaccines (and associated diluents) are vaccines (and diluents) for Marek's disease and Newcastle disease.

In some embodiments, two or more different poultry vaccines (e.g. a vaccine for Marek's disease and a vaccine for Newcastle disease) can be administered in the same vaccination protocol, either together in combination, or separately. This option is likely to be particularly appropriate where the same vaccine diluent is suitable for the different vaccines. For example, the preferred diluents described herein, for example the diluent of Example 1 and related diluents, are believed to be appropriate for use with both vaccines for Marek's disease and vaccines for Newcastle disease.

Particularly preferred vaccines for Marek's disease comprise a strain of turkey herpes virus (HVT), which is antigenically similar to Marek's disease virus (MDV) or a strain of chicken herpes virus, or a combination thereof. Such vaccines (and appropriate diluents) are well known in the art and commercially available, for example from Merial Select, Inc. However, other vaccines for Marek's disease can also be used in the present invention, for example based on live or attenuated versions of the Marek's disease virus, e.g. based on any of the three serotypes of MDV, or combinations thereof, for example gallid herpesvirus type 3 is serotype 2 of MDV and turkey herpes virus is serotype 3 of MDV. Rispens CVI 988 is an exemplary strain of chicken herpes virus.

A particularly preferred strain of turkey herpes virus for use in the present invention is an FC126 strain. A particularly preferred strain of chicken herpes virus is an SB1 strain. Combinations of said strains can also be used.

Many poultry vaccines are available (e.g. commercially available) for Newcastle disease and any of these may be used in the present invention. Many alternative strains of Newcastle disease virus are used in the various vaccines. For example, exemplary strains include V4, V4-HR, I-2, F, B-1 or the La Sota strain of Newcastle disease virus, or combinations thereof. In some embodiments vaccines based on the F or B-1 strains are preferred, for example based on the F strain for in ovo vaccination protocols.

As mentioned above, the vaccines for use in the present invention should preferably be appropriate for in ovo administration and also be compatible with an appropriate probiotic bacteria such that the probiotic bacteria can be diluted with the specific vaccine diluent for the vaccine concerned and used together in a combined therapy (vaccination protocol) such that the probiotic bacteria still functions as a probiotic to a useful extent and the vaccination capability of the vaccine is preserved to an effective extent.

Appropriate diluents for use with particular poultry vaccines will be available to the skilled person, as a diluent with an appropriate composition is generally supplied with the vaccine concerned. In this way, the vaccine diluent is tailored to the vaccine in question so that the stability and effectiveness of the vaccine is not affected. Thus, an appropriate diluent should not affect the stability or vitality (e.g. titre) of the vaccine culture in a negative way. The diluent is preferably free of chlorine, antibiotics, antimicrobials, or any other agent which may be harmful to the vaccine organisms and is at an appropriate pH so as not to be harmful to the live vaccine organisms. In preferred embodiments the vaccine diluent has a pH of between 6.9 and 7.3. (The diluent should also of course not be detrimental to the function of the chosen probiotic either).

In some preferred embodiments of the invention, the vaccine diluent is not saline or phosphate buffered saline (PBS). In other embodiments, the vaccine diluent is not a probiotic bacteria fermentation medium or growth medium. In other embodiments of the invention, the vaccine diluent is not water, for example is not sterile water or distilled water.

In preferred embodiments of the invention, for example where the vaccine in question is a vaccine for Marek's disease or for Newcastle disease and the vaccine diluent is a diluent for a vaccine for Marek's disease or for Newcastle disease, said vaccine diluent comprises one or more of the components selected from the group consisting of sucrose, NZ Amine AS, dibasic potassium phosphate and monobasic potassium phosphate. More preferably, said vaccine diluent comprises two or more, three or more, or all of these components. Optionally, said vaccine diluent may further comprise phenol red or some other pH indicator. In preferred embodiments the vaccine diluent has a pH of between 6.9 and 7.3. In some embodiments the vaccine diluent has a solids content of between 6.0% and 8.0%, for example at or around 6.8% or 7.0%.

A particularly preferred vaccine diluent recipe for use in the present invention is provided in Example 1.

Other preferred vaccine diluents for use in the present invention have sucrose as the main component, for example comprise a sucrose content of 2% to 10%, for example 3% to 7%, e.g. of around 5%.

Other preferred vaccine diluents have N.Z. Amine AS as a component, preferably a second component, for example comprise an N.Z. Amine AS content of 0.25% to 2.75%, for example 1.0% to 2.0%, e.g. of around 1.5%.

Other preferred vaccine diluents have potassium phosphate as a component, preferably as a second or third component, for example comprise a total potassium phosphate content of 0.08% to 0.26%, for example 0.1% to 0.2%, e.g. of around 0.17%. The potassium phosphate can be made up of dibasic or monobasic potassium phosphate, or a mixture of the two. Preferred content of dibasic potassium phosphate is for example 0.06% to 0.20%, e.g. 0.10% to 0.17%, e.g. around 0.125%. Preferred content of monobasic potassium phosphate is for example 0.02% to 0.07%, e.g. 0.03 to 0.06%, e.g. around 0.05%.

Although the compositions of the invention comprising the strains of probiotic bacteria and a vaccine diluent are suitable for use in an in ovo vaccination protocol for poultry, as will be described in more detail elsewhere herein, the probiotic bacteria containing composition of the invention can be administered in combination with (together as a combined preparation) or separately from the vaccine composition.

Thus, in some aspects of the invention, the composition comprising the probiotic bacteria and the vaccine diluent may further comprise the poultry vaccine for use in said vaccination protocol. In such embodiments, in order for all the components to be compatible with and to not negatively affect the function of the others to a problematic extent, the poultry vaccine and probiotic bacteria are provided or combined together in the same vaccine diluent. In other words, the probiotic bacteria is present in the same vaccine diluent as the poultry vaccine and the probiotic bacteria is selected to be suitable for and compatible with said poultry vaccine and associated diluent.

As described elsewhere herein, in ovo administration, conveniently by injection, is a preferred and advantageous form of vaccine administration and the present invention concerns in ovo vaccination protocols for poultry. Such protocols and means and methods of in ovo vaccination are well known and described in the art. One of the aims of in ovo vaccination is that the in ovo administration of an active entity (e.g. a probiotic bacteria or a vaccine in the present case) results in this active entity (and indeed any entity administered) being transferred via the poultry embryo to the gastrointestinal (GI) tract of the poultry when it is hatched.

Thus, the compositions comprising the probiotic bacteria and the vaccines (either together or separately) as described herein are administered to embryonated or fertilised eggs at the appropriate dose and at the appropriate time point to enable the probiotic bacteria and the vaccines to be present at an appropriate and functional amount in the GI tract of the poultry upon hatching. In particular, for the probiotic bacteria, the doses and timing of administration to the egg are selected such that the probiotic bacteria can result in colonisation of the GI tract upon hatching of the poultry or shortly after (e.g. up to seven days after hatch). This is important to ensure that the health benefit of the probiotic bacteria can be achieved in the poultry.

Any appropriate sites of administration or injection to the embryonated egg can be used in order to obtain successful in ovo delivery and passage to the GI tract of the resulting hatched poultry. However, particularly preferred sites of administration are administration to the air cell or the amniotic fluid of the egg. Such administration is generally by way of injection. Such administration can be carried out in any appropriate way, for example commercial machines are available for large scale automated in ovo administration, or the administration can be carried out manually.

Appropriate time points for administration will vary depending on the type of poultry egg concerned. However, a preferred time point is around 2 days before hatch and a person skilled in the art can readily determine the appropriate timings to achieve this. For example, for chicken eggs, administration can take place when the embryonated eggs are 18-19 days old.

Appropriate dosages of the probiotic bacteria and the vaccines to be used in the invention can be readily determined by a person skilled in the art.

For example, a dosage and administration regime is chosen such that the probiotic bacteria administered to the embryonated egg in accordance with the present invention can be transferred to the hatched poultry in an appropriate amount to colonize the GI tract and to give rise to the desired therapeutic effects or health benefits. Thus, preferably said dosage is a therapeutically effective dosage which is appropriate for the type of poultry being treated. For example, doses of $10^5$ to $10^8$ total CFUs of bacteria per embryonated egg may be used. Preferred doses are $5\times10^5$ to $7\times10^6$ CFU, more preferably $2\times10^6$ to $7\times10^6$ or $5\times10^6$ CFU per egg, most preferably at or around $2\times10^6$ CFU per egg. Any volume suitable for in ovo administration may be used but typical volumes are 50-100 µl per embryonated egg.

Similarly, a dosage and administration regime is chosen for the vaccine component such that the poultry vaccine administered to the embryonated egg in accordance with the present invention can be transferred to the hatched poultry in an appropriate amount to give rise to the desired vaccination/protection effects for the disease and vaccine in question. Appropriate dosages for the in ovo administration of poultry vaccines will be well known and described in the art, for example will be indicated in the instructions supplied with or otherwise associated with the commercially supplied vaccine. Alternatively, appropriate doses for in ovo administration can be readily determined by the skilled man.

Thus, in order to obtain the benefits of the invention, after the in ovo administration, the eggs are generally incubated to the point of hatch, after which the poultry are allowed to grow to adults (or any other appropriate stage) but with the health benefits of the probiotic bacteria, together with the selected vaccine, that has been administered in ovo. Thus, not only are the poultry which develop from these eggs provided with the benefit of the probiotic bacteria which has been administered in ovo, but they are also provided with the benefits of the vaccination protocol, i.e. vaccination against the selected diseases.

Thus, a yet further aspect of the invention provides an embryonated poultry egg comprising a culture of probiotic bacteria (preferably *Lactobacillus* bacteria), wherein the probiotic containing composition of the invention as described elsewhere herein (for example a composition comprising a strain of a probiotic bacteria and a vaccine diluent, optionally further comprising a poultry vaccine), is or has been administered to said embryonated egg.

As described elsewhere herein said composition is preferably administered into the air cell or the amniotic fluid of the egg.

Preferred poultry vaccines, diluents, and preferred and alternative probiotic bacteria for use in such aspects are as described elsewhere herein.

As can be seen from the above discussion, the present invention is concerned with in ovo vaccination protocols for poultry and, in particular, combination therapies using probiotic bacteria and poultry vaccines in which both actives can exert their biological or physiological effects.

Thus, one aspect of the present invention provides a (one or more) strain of *Lactobacillus* probiotic bacteria and a poultry vaccine for use in the in ovo vaccination of poultry, wherein said strain and said vaccine are administered to an embryonated poultry egg.

The probiotic bacteria and the poultry vaccine are selected to be compatible with each other (for example the probiotic bacteria is selected to be compatible with the vaccine of choice) such that negative interference between the probiotic bacteria and the vaccine is reduced or minimised. As discussed elsewhere herein, this finding that vaccine administration and probiotic treatment can be combined in poultry given the sensitivities of the actives involved was surprising. A key way by which the inventors found that this can be achieved is by the probiotic bacteria being present in or diluted in the same diluent as the vaccine diluent for the particular vaccine concerned or chosen.

Thus, alternatively viewed, the present invention provides a composition comprising a strain of *Lactobacillus* probiotic bacteria and a vaccine diluent for use in the in ovo vaccination of poultry, wherein said composition is administered to an embryonated poultry egg, wherein said use further comprises the administration of a poultry vaccine comprising the same vaccine diluent.

Alternatively viewed, the present invention provides a (one or more) strain of *Lactobacillus* probiotic bacteria and a vaccine diluent, and a poultry vaccine comprising the same vaccine diluent, for use in the in ovo vaccination of poultry wherein said probiotic bacteria and vaccine is administered to an embryonated poultry egg.

Alternatively viewed, the present invention provides a composition comprising a strain of *Lactobacillus* probiotic bacteria and a vaccine diluent for use in the in ovo vaccination of poultry by combined, sequential or separate administration with a poultry vaccine comprising the same vaccine diluent, wherein said composition and vaccine is administered to an embryonated poultry egg.

There is further provided a product comprising a strain of *Lactobacillus* probiotic bacteria, a poultry vaccine and a vaccine diluent (for the poultry vaccine) as a combined preparation for separate, simultaneous or sequential use in the in ovo vaccination of poultry.

Thus, yet further aspects of the invention provide the use of a (one or more) strain of *Lactobacillus* probiotic bacteria and a poultry vaccine in the manufacture of a medicament for use in the in ovo vaccination of poultry, wherein said strain and said vaccine are administered to an embryonated poultry egg.

Thus, alternatively viewed, the present invention provides the use of a composition comprising a strain of *Lactobacillus* probiotic bacteria and a vaccine diluent in the manufacture of a medicament for use in the in ovo vaccination of poultry, wherein said composition is administered to an embryonated poultry egg, wherein said use further comprises the administration of a poultry vaccine comprising the same vaccine diluent.

Alternatively viewed, the present invention provides a (one or more) strain of *Lactobacillus* probiotic bacteria and a vaccine diluent, and a poultry vaccine comprising the same vaccine diluent, in the manufacture of a medicament for use in the in ovo vaccination of poultry wherein said probiotic bacteria and vaccine is administered to an embryonated poultry egg.

Alternatively viewed, the present invention provides a composition comprising a strain of *Lactobacillus* probiotic bacteria and a vaccine diluent in the manufacture of a medicament for use in the in ovo vaccination of poultry by combined, sequential or separate administration with a poultry vaccine comprising the same vaccine diluent, wherein said composition and vaccine is administered to an embryonated poultry egg.

Thus, yet further aspects of the present invention provide a method of in ovo vaccination of poultry, comprising the step of administering a (one or more) strain of *Lactobacillus* probiotic bacteria and a poultry vaccine to an embryonated poultry egg.

Thus, alternatively viewed, the present invention provides a method of in ovo vaccination of poultry, comprising the step of administering a composition comprising a strain of *Lactobacillus* probiotic bacteria and a vaccine diluent to an embryonated poultry egg, wherein said method further comprises the administration of a poultry vaccine comprising the same vaccine diluent.

Alternatively viewed, the present invention provides a method of in ovo vaccination of poultry, comprising the step of administering a (one or more) strain of *Lactobacillus* probiotic bacteria and a vaccine diluent, and administering a poultry vaccine comprising the same vaccine diluent, to an embryonated poultry egg.

Alternatively viewed, the present invention provides a method of in ovo vaccination of poultry by combined, sequential or separate administration of (i) a composition comprising a strain of *Lactobacillus* probiotic bacteria and a vaccine diluent, and (ii) a poultry vaccine comprising the same vaccine diluent, wherein said composition and vaccine is administered to an embryonated poultry egg.

There is further provided a product comprising a strain of *Lactobacillus* probiotic bacteria, a poultry vaccine and a vaccine diluent (for the poultry vaccine) as a combined preparation for separate, simultaneous or sequential use in a method for the in ovo vaccination of poultry.

The administration of active ingredients (e.g. probiotic bacteria and vaccines) in said methods of treatment and uses of the invention is carried out in pharmaceutically effective amounts, to poultry in need of treatment.

The aim of such medical uses and methods of treatment is that the beneficial effects of the probiotic are observed in the poultry which is hatched from the embryos within the egg and also that the vaccination with the poultry vaccine is effective.

Preferred poultry vaccines, diluents, and preferred and alternative probiotic bacteria are as described elsewhere herein for other aspects of the invention. Thus, more than one strain of probiotic bacteria can be used in such embodiments.

The combination therapy of the present invention and the fact that the probiotic bacteria component and the vaccine components are compatible with each other means that the three components, i.e. the probiotic bacteria, the vaccine and the vaccine diluent (wherein preferably the same vaccine diluent is used for both the probiotic bacteria and the vaccine), can be co-administered in combination in the same composition. Alternatively, the probiotic bacteria component can be administered separately from the vaccine component.

As described elsewhere herein, the probiotic bacteria component must be compatible with the poultry vaccine component. This is preferably and advantageously achieved by using the same diluent for both components. As the vaccine component is particularly sensitive to the diluent which is used, in preferred embodiments, the probiotic bacteria will be administered in the same diluent as the vaccine diluent. For practical reasons, time and cost saving reasons and not least for risk of contamination reasons, multiple in ovo injections should generally be avoided. However, if the probiotic bacteria is present in an alternative diluent (liquid media) which is not incompatible with the vaccine or vaccine diluent then the probiotic bacteria need not be administered in the same diluent as the vaccine diluent and can be administered in its own media either separately or in combination with the vaccine and vaccine diluent (e.g. after mixing).

A skilled person will readily be able to determine whether a vaccine and its diluent are compatible with a probiotic bacteria to an appropriate extent to be useful in the present invention. For example, ultimately both the probiotic component and the vaccine component need to be able to retain sufficient function in the presence of each other to exert a useful effect in the poultry to which they are administered in accordance with the present invention.

Preferably, to be compatible, the probiotic bacteria should not effect, not significantly effect, or not inhibit below a useful extent, the ability of the vaccine to have a vaccination effect in poultry. For a live vaccine this can for example be tested by assessing the effect of the probiotic bacteria and its diluent (liquid media, for example the same diluent as the vaccine) on the cell viability or titre of the vaccine (e.g. the viruses making up the vaccine). An appropriate assay is described in the Examples section where for example it is shown that at 1 hour or 2 hours post reconstitution the cell viability of the vaccine (in this case the HVT or SB-1 strain of a Marek's vaccine) in the presence of the probiotic bacteria (and test diluent) is at least 95% of the level seen when the probiotic bacteria is absent (i.e. when the vaccine and its diluent are present alone). In other embodiments with different vaccines and/or probiotic bacteria, levels of at least 70%, 80%, 90%, or 95% cell viability might be appropriate but this can be readily determined by a skilled person, for example by also including a comparison with a control probiotic bacteria sample, for example a control probiotic bacteria sample with an incompatible diluent. If such a control is used then a % of cell viability which is higher with the test probiotic sample than with the control probiotic sample would be appropriate.

When titre is used as a measurement of compatibility, then again an appropriate assay is described in the Examples section, where for example it is shown that the virus titre at 0 hours (immediately after reconstitution) when the probiotic bacteria (and test diluent) is present is not effected or is at least 75%, 80%, 85%, 90% or 95% of the level seen when the probiotic bacteria is absent (i.e. when the vaccine and its diluent are present alone). Such titres can also be measured at alternative time points, e.g. 1 hour after reconstitution, although generally an earlier time point is preferred. In other embodiments with different vaccines and/or probiotic bacteria bacteria, other % levels of retained titre might be appropriate, but this can be readily determined by a skilled person. Again in such tests for titre it can also be helpful to for example include a comparison with a control probiotic bacteria sample, for example a control probiotic bacteria sample with an incompatible diluent. If such a control is used then a % of titre which is higher with the test probiotic sample than with the control probiotic sample would be appropriate.

In embodiments where the administration of the probiotic and the vaccine components are anyhow made separate or sequential, it is preferred that the administrations are made within a reasonable timeframe of each other. For example, the separate administrations are preferably made within hours (e.g. one hour) or minutes (e.g. within 15 or 30 minutes) of each other, most preferably within as short a timeframe as possible (including simultaneous or effectively simultaneous administration) depending on the particular method of in ovo administration which is used.

In preferred embodiments where the probiotic bacteria and the vaccine components are co-administered in a single composition, preferably with a single diluent corresponding to the vaccine diluent, composition should be administered to the embryonated poultry eggs as soon as possible after the probiotic component and the vaccine component have been mixed together. Thus, it is generally preferred that administration takes place to the eggs immediately after the probiotic bacteria is mixed with the vaccine, for example within one hour or two hours after mixing, more preferably within one hour.

The health benefits of a particular probiotic bacteria to poultry would be well known and recognised to a person skilled in the art. Indeed, as well as the compatibility with the vaccine, this would be one of the selection criterion to choose an appropriate probiotic bacteria for use in the methods of the invention. Thus, for example the probiotic bacteria administration can result in reduced levels (e.g. CFUs) of enterobacterial pathogens (e.g. *E. coli* and/or *Salmonella*) in the GI tract of the poultry, or colonization (or increased colonization) of the poultry with said probiotic bacteria, for example in comparison to poultry which had not been administered with the probiotic bacteria in question.

Probiotic bacteria have also been shown to have a positive effect on hatchability (the percentage of eggs set to hatch that in fact hatch) and also a positive effect on mortality (e.g. early poult mortality), for example 7 day mortality. In the present Examples for example, it is shown that *L. reuteri* injected eggs result in an increased percentage of live embryos upon hatch (compared to untreated or control treated embryos) and also an increased percentage of embryos/poults surviving at day 7 after hatch (compared to untreated or control treated embryos).

Preferably such increases (and indeed other increases or positive effects or decreases or reduced effects mentioned elsewhere herein) are measurable increases (or decreases, etc., as appropriate), more preferably they are significant increases (or decreases, etc., as appropriate), preferably statistically significant, for example with a probability value of <0.05, when compared to an appropriate control level or value.

Preferred probiotic bacteria for use in the present invention have a positive effect on hatchability (or less preferably do not have a negative effect on hatchability) for example compared to untreated or control treated embryos. Preferred hatchability percentages observed with the probiotic bacteria are at least 95% or at least 98%.

Preferred probiotic bacteria for use in the present invention have a positive effect on mortality, e.g. 7 day mortality (or less preferably do not have a negative effect on mortality) for example compared to untreated or control treated embryos. Preferred mortality (e.g. 7 day mortality) percentages observed with the probiotic bacteria are at least 85%, 90% or 95%.

The administration of probiotic bacteria to poultry has also for example been shown to counteract various pathogenic challenges for example by reducing the level (e.g. CFUs) of enterobacterial pathogens such as *salmonella* or *E. coli* (for example compared to levels observed the absence of probiotic bacteria or the presence of a control probiotic bacteria). *E coli* in poultry are for example known to be associated with a reduction in hatchability and early poult mortality.

In addition, an important advantage is that the administration of a probiotic in accordance with the present invention can remove the need for administration of an antibiotic such as gentamicin. Thus, preferred methods and uses of the invention do not involve the administration of an antibiotic.

The present invention can thus be used to treat or prevent any disease or condition in a poultry embryo, poult or adult bird which can benefit from treatment with probiotic bacteria. Exemplary conditions for treatment are discussed above. The present invention can also be used for the treatment or prevention of a health-related disease or condition associated with poultry embryos or poults born with a non-optimal intestinal flora or microbiome.

The therapeutic uses of the present invention as described herein generally result in the reduction or alleviation of the relevant disease or condition, or symptoms thereof. Such reduction or alleviation of disease or conditions or symptoms thereof can be measured by any appropriate assay depending on the disease in question. The reduction or alleviation of disease, condition, or symptoms is preferably clinically significant. Preferably the reduction or alleviation of disease, condition or symptoms is statistically significant, preferably with a probability value of <0.05. Such reduction or alleviation of disease, condition or symptoms are generally determined compared to an appropriate control individual or population, for example healthy poultry or untreated or placebo treated poultry.

As will be clear from the disclosure elsewhere herein, the methods and uses of the prevent invention are suitable for prevention of diseases as well as treatment of diseases. This is particularly the case for the vaccination effects of the invention, which are based on and imply prevention of disease or at least a reduced incidence or increased control of disease. Thus, prophylactic treatment is also encompassed by the invention. For this reason in the methods and uses of the present invention, treatment also includes prophylaxis or prevention where appropriate. Preferred aspects where prevention is envisaged are discussed herein and include the vaccination aspects.

There are many diseases that can be vaccinated against in poultry and any of these are appropriate for the present invention providing that the vaccine can be administered in ovo. Preferred diseases and vaccines are discussed elsewhere herein.

The methods and uses of the present invention are suited to any type of poultry, e.g. any type of domesticated or commercially bred bird or fowl such as chickens, turkeys, geese or ducks. Turkeys or chickens are preferred, chickens more preferred.

In a further aspect of the invention kits or pharmaceutical packs are provided. Thus, the present invention provides a kit or pharmaceutical pack comprising
(i) a strain of *Lactobacillus* probiotic bacteria;
(ii) a poultry vaccine and optionally (iii) a single vaccine diluent which is suitable for use with (i) and (ii).

Preferred poultry vaccines, diluents, and preferred and alternative probiotic bacteria are as described elsewhere herein for other aspects of the invention. Thus, more than one strain of probiotic bacteria can be used in such embodiments, in which case they are generally provided as separate components of the kit or pack. Preferably such kits or packs are for use in the methods and uses of the present invention, for example are for use in the in ovo vaccination of poultry. The kit or pack can of course also comprise instructions for administration or use of the kit/pack.

The invention will be further described with reference to the following non-limiting Examples:

EXAMPLES

Example 1 Manufacture of a Frozen In Ovo Composition

The in ovo-product of the present invention can be in both frozen form or in freeze dried form. Commercially it is called Reuteri-InOvo™. It can be produced from small batches to larger volumes. This is an example of the production of frozen products in vials:

*Lactobacillus reuteri* strain T-1, ATCC 55149 (isolated from turkey) and strain 11284 ATCC 55148 (isolated from chicken) are used. (The strains can be acquired from ATCC in Manassas, Va., USA) The two strains are grown separately in two different fermentors and then mixed before the cell concentration.

The frozen vials should be stored at −80° C.

Materials and Methods

Definitions

Bacteria slurry=the cell suspension after cell concentration and washing

Bacteria concentrate=the bacteria slurry after the addition cryo protectant

Fermentation

Fermentor: CH014 (K3)—for the 11284, CH07 (LF2)—for the T1

| Substrate: | |
|---|---|
| Glucose monohydrate | 66.0 gram/litre |
| Yeast extract | 24.1 gram/litre |
| Soy peptone A2 | 20.0 gram/litre |
| Na-acetate × 3H$_2$O | 5.0 gram/litre |
| di-ammonium citrate | 2.0 gram/litre |
| K$_2$HPO$_4$ | 80 mg/litre |
| MgSO$_4$ × 7H$_2$O | 200 mg/litre |
| MnSO$_4$ × H$_2$O | 200 mg/litre |
| Tween 80 | 1.0 gram/litre |

Volume: 10 liter—in CH014, 5 liter—in CH07

Sterilisation: 121° C. for 25 minutes, glucose sterilised separately.

Cell Concentration

The cells are concentrated on a cross flow micro filter from Sartocon (0.22 µm, 0.6 m$^2$). The concentration factor (CF) is about 14 and the concentrate is washed with the vaccine diluent. The slurry has an estimated solids content of about 6% from the cells and 6.8% from the diluent giving a total solids content of about 13%.

Vaccine Diluent:

| Composition: | |
|---|---|
| Sucrose | 51.25 g/litre |
| N.Z. Amine AS | 15.00 g/litre |
| Potassium phosphate, dibasic | 1.25 g/litre |
| Potassium phosphate, monobasic | 0.46 g/litre |
| Phenol red | 0.01 g/litre |
| Solids content | 6.8% |
| pH | 6.9-7.3 |

Filling

The filling of the first batch is done by hand with a manual pipette. From the second batch a Multipette from Eppendorf for repetitive pipetting, with a sterile magazine containing 25 ml, is used to speed up the filling. All vials are filled with 1.00 ml. It takes about 30 seconds to empty the magazine.

The bacteria concentrate is kept in a bottle at about +7° C. in an ice/water bath during the filling. Every 5 minute the bottle is removed from the water and put on a magnetic stirrer for a couple of minutes. After that a portion of the concentrate is filled into a 100-ml beaker that is constantly on a magnetic stirrer but without cooling. This arrangement is used to keep the cell concentrate refrigerated but also in motion to minimise the sedimentation of the cells. Before filling the vials a label is put on and after filling the cap is screwed on by hand.

The filling was done in a LAF-bench in a clean room.

Freezing

The freezing and storing is done at −80° C. The −80° products are first frozen at −40° and then after 1-4 days transferred to −80° C.

Analysis

All analyses for *Lactobacillus reuteri* is done on MRS-cystein agar. The samples are plated on top of the agar and incubated anaerobically for two days at +37° C.

The frozen samples are thawed and dissolved in MRS broth and the serial dilutions are done with 0.9% NaCl. In all stability test the start analysis is done after 3-5 days post freezing.

Summary

The concentration per vial is too low but can be increased by using bigger fermentors since the concentration factor is limited by the size of the filter.

The hygienic standard is good for the produced vials but BGF can not analyse all the contaminants that are in the specification.

There are big variations in the concentration over time probably due to sedimentation of the cells during filling.

The stability at −80° C. varies in the order of 60-124% after 45 days and 63-160% after 90 days.

There are indications that the stability is negatively affected by storing the bacteria concentrate over night at +8° C. before filling the vials.

There are indications that the chicken strain has a lower stability than the turkey strain.

A maximal production of about 1.250 vials per month can be run without investing in new laboratory fermentors. Filling equipment must also be bought for bigger production volumes.

The frozen vials should be stored at −80° C.

Example 2 Hatchability

Eggs of chickens are aseptically punctured above the air cell with a needle, preferably about 2 days before hatch. With a syringe and needle, 100 ul of a mixed 50/50 suspension of *Lactobacillus reuteri*, strain T-I (isolated from turkeys) or strain 11284 (isolated from chickens) diluted into vaccine diluent for Marek's vaccine from Merial Inc, (Gainswille, Ga., USA), containing about $10^5$, $10^7$, or $10^8$ cells in total of the strains, is injected into the air cell.

Table 1 shows the effect on hatchability with varying levels of *Lactobacillus* inoculation. The data presented in Table I for chickens show that pure cultures of *Lactobacillus reuteri* can be successfully introduced into viable poultry eggs without effecting the hatchability of the eggs negatively.

TABLE I

| TREATMENT | % LIVE EMBRYOS AT HATCH/ % OF SURVIVORS AT DAY 7 |
|---|---|
| Untreated embryos | 94/80 |
| Phosphate injected (control) | 93/81 |
| *L. reuteri* air cell injected, $10^5$ CFU | 98/88 |
| *L. reuteri* air cell injected, $10^7$ CFU | 100/95 |
| *L. reuteri* air cell injected, $10^8$ CFU | 94/83 |

This in ovo method serves as a new means for introducing defined beneficial microorganisms such as a pure strain of *Lactobacillus reuteri*, into the gastrointestinal tract of poultry at an early stage. The embryonic chick or poult is immersed in amniotic fluid which is in contact with the gastrointestinal tract. Thus, the microorganism inoculated in ovo can become established in the bird's gastrointestinal tract.

Example 3 Field Test

Industrial *Lactobacillus reuteri* administration by in ovo injection: Colonization at hatch.

*Lactobacillus reuteri* is used as probiotic in man and animals. It has been shown that early colonization improves the efficacy of this probiotic. Previous reports of studies have shown that in ovo *L. reuteri* administration is safe and results in good colonization. The potential of early colonization by in ovo injection has been demonstrated in chickens and poults. *L. reuteri* administration in ovo increases its rate of intestinal colonization and decreases the colonization of *Salmonella* and *Escherichia coli* in both chicks and poults. In ovo administration of probiotics with competitive exclusion activity is of highly relevant because there is a worldwide movement to reduce antibiotics in poultry due to increased microbial resistance to antibiotics. We report the results of three trials of in ovo *L. reuteri* administration to chicken embryos utilizing the "Inovoject" system (Embrex, Durham, N.C., USA).

Objective:

The aim of this study was to determine *L. reuteri* in ovo administration in commercial scale in the presence and absence of gentamicin. Modern equipment for in ovo injection and *L. reuteri* production with state of the art technology demanded for this application was used for the study.

Procedures:

The breed used throughout all the trials was Cobb/Cobb. Chicks were placed in houses holding approximately 21,000 birds each.

Aseptically produced concentrated cell inoculum for in ovo application was suspended in Marek's disease vaccine diluent and frozen at $-70°$ C., or lower temperature, until use. The concentrated preparation/innoculum was added to further Marek's disease vaccine diluent. The dilution was made in a way to deliver the desirable colony forming units (CFU) of *L. reuteri* in 50 µl volume. This volume was injected into each embryonated egg at transfer from the setters to the hatchers by means of the "inovoject" technology. Depending of the objective of the study, different levels of *L. reuteri* (1E+6 to 5E+6) were suspended in the 50 µl. Colonization was evaluated at hatch and in some occasions at 4, 7 days after hatch. At each sampling date chicks were sampled and the cecum aseptically removed, frozen and stored at $-70°$ C. until analysis. One week mortality was also recorded as a performance indicator.

Three Trials were Conducted as Part of the Study:

(i) Five treatments were included in this trial: 1 negative control and 4 levels of *L. reuteri*, 5E+5, 1E+6, 2E+6 and 5E+6 CFU per embryonated egg. Gentamicin was included in the vaccine preparation. Twenty eight thousand eggs were injected with each *L. reuteri* level and 20,500 birds of each treatment were placed separated houses.

(ii) Four treatments were included in this trial: 1 negative control and 3 levels of *L. reuteri*, 2E+6, 5E+6 and 7E+6 CFU per embryonated egg. Gentamicin was not included in the vaccine preparation. Twenty eight thousand eggs were injected with each *L. reuteri* level and 20,500 birds of each treatment were placed separated houses.

(iii) Two treatments were included: 1—negative control and 2—product (*L. reuteri* mixture at 2E+6 CFU per embryonated egg). Gentamicin was not included in the vaccine preparation. 150,000 eggs were injected in each treatment group. Twenty one thousand birds were placed per chicken house. Seven houses were assigned to each treatment group.

Results:

Trial (i). At day of hatch no colonization was detected by direct plating in any of the *L. reuteri* treatment levels. However, upon enrichment *L. reuteri* was detected at the 2E+6 level and in the 2E+6 and 5E+6 levels at 3 days of age. The killing effect of gentamicin was demonstrated during the holding time in the vaccine preparation. Trial (ii). Colonization at hatch was found to be dose dependent: The percentage of birds colonized with *L. reuteri* was 0, 93, 73 and 33 ($p<0.05$, control vs. treatments); and the average number of *L. reuteri* found in the cecum was 1.1, 4.1, 3.8, and 3.0 $\text{Log}_{10}$ CFU ($p<0.01$) for the negative control, 2E+6, 5E+6 and 7E+6 CFU dose per embryonated egg, respectively. Seven day mortality was 1.8%, 0.75%, 0.76% and 1.15% for the same treatment groups.

Trial (iii). The results at hatch, expressed as average of the 7 houses for the control and product groups are: 0 VS. 82% of colonized birds ($p<0.05$) and 0.18 VS. 4.3±1.1 $\text{Log}_{10}$ CFU/cecum ($p<0.01$). Seven day mortality are 1.55 VS. 1.36%, respectively Conclusions.

The findings show that:

*Lactobacillus reuteri* in ovo injection results in good colonization measured as percent of chicks colonized at hatch and number of *L. reuteri* per cecum.

Thus, *L. reuteri* colonization via in ovo injection is effective and it is dose dependent. The optimum dose is found to be 2E+6 CFU/embryonated egg.

The "inovoject" system was found to be effective for co-injection of Marek's disease vaccine diluent and *L. reuteri* when the probiotic was frozen in vaccine diluent.

Gentamicin negatively affects *L. reuteri* colonization via in ovo injection.

*L. reuteri* in ovo administration and subsequent colonization decreases one week mortality, Therefore, it is possible to avoid the use of gentamicin.

Example 4 Vaccine Compatibility Using the Probiotic Produced as by the Invention Herein The aim of this study is to investigate the effect of adding a probiotic composition, comprising *Lactobacillus reuteri* strain T-I (isolated from turkeys) and strain 11284 (isolated from chickens) diluted into vaccine diluent for Marek's vaccine from Merial Inc, (Gainswille, Ga., USA), to common used vaccines for poultry (HVT and SB-1, both used for treatment of Marek's disease). As a control the same a probiotic composition is used which is diluted in water (sterile water) before freezing instead of being diluted in vaccine diluent.

Procedure:
- Dilution of three vaccine vials (HVT and SB-1 strains) (2,000 doses each: 6,000 doses total) into three diluent bags (400 mL each: 1200 mL total). Vaccine and diluent are provided by Merial (Serial # DM798 EXP date April-16)
- 400 mL of the reconstituted vaccine remains as such and 400 mL is mixed with one vial of probiotic, in one case according to the invention herein, and 400 mL is mixed with the control probiotic.
- Plaque assay for titrations are done in triplicates. Each titration has four serial 10-fold dilutions.
- Titrations are done at time 0 (as soon as the vaccine is reconstituted) and 1 hour after reconstitution
- Cell viability is evaluated 1 h and 2 h after the vaccine is reconstituted
- HVT plaques are counted at 3 days post inoculation
- SB-1 plaques are counted at 5 days post inoculation Results:

| Cell viability (%) | | |
|---|---|---|
| Treatment | 1 h post reconstitution | 2 h post reconstitution |
| HVT | 93 | 83 |
| HVT + probiotic | 92 | 82 |
| HVT + control probiotic | 87 | 79 |
| SB-1 | 95 | 84 |
| SB-1 + probiotic | 94 | 81 |
| SB-1 + control probiotic | 86 | 78 |

| HVT titration | | | | | |
|---|---|---|---|---|---|
| Time after reconstitution | Treatment | Replicate 1 | Replicate 2 | Replicate 3 | Average |
| 0 h | HVT | 1230 | 985 | 1415 | 1210 |
|  | HVT + prob | 970 | 1265 | 1015 | 1083 |
|  | HVT + p-c | 830 | 935 | 880 | 882 |
| 1 h | HVT | 1080 | 820 | 860 | 920 |
|  | HVT + prob | 940 | 880 | 810 | 877 |
|  | HVT + p-c | 890 | 815 | 770 | 825 |

| SB-1 titration | | | | | |
|---|---|---|---|---|---|
| Time after reconstitution | Treatment | Replicate 1 | Replicate 2 | Replicate 3 | Average |
| 0 h | SB-1 | 1430 | 1000 | 945 | 1125 |
|  | SB-1 + prob | 1165 | 1240 | 1105 | 1170 |
|  | SB-1 + p-c | 925 | 1002 | 978 | 968 |
| 1 h | SB-1 | 1155 | 1115 | 830 | 1033 |
|  | SB-1 + prob | 660 | 705 | 550 | 638 |
|  | SB-1 + p-c | 540 | 580 | 510 | 543 |

Conclusion:

The probiotic composition has no effect on cell viability when the vaccine diluent is used. In contrast, when water is used as a diluent (control probiotic), lower cell viability is observed. Addition of the probiotic diluted in the vaccine diluent (HVT+prob or SB-1+prob) has no effect on HVT titers at times 0 and times 1 or in titers of SB-1 at time 0. However, the addition of the probiotic diluted in the vaccine diluent reduces the titers of SB-1 when titers are measured 1 hour after reconstitution. These results show that water is significantly less compatible with the vaccine than the vaccine diluent, or in other words that water as a diluent has a negative effect on cell viability and titre compared to the use of vaccine diluent. In this experiment, even a small amount of water (a 1 ml vial of probiotic diluted in water added to a total volume of 400 ml vaccine diluent) had a negative effect on cell viability and titre of the vaccine. The negative effect of the water is also seen immediately (i.e. at 0 h after reconstitution) meaning that such effect is rapid as well as negative compared to the results where vaccine diluent is used. Ideally however, for the best results, in ovo administration of the probiotic in vaccine diluent should take place as soon as possible after the probiotic has been mixed with the reconstitued vaccine.

The invention claimed is:

1. A method of administering to an avian subject in ovo an effective dose of a strain of *Lactobacillus* probiotic bacteria and a vaccine for Marek's disease and/or Newcastle disease in a vaccine diluent, comprising:
    washing and concentrating the strain of *Lactobacillus* probiotic bacteria with the vaccine diluent, wherein the vaccine diluent comprises one or more of the components selected from the group consisting of: sucrose, N.C. Amine AS, dibasic potassium phosphate and monobasic potassium phosphate;
    suspending a strain of turkey herpes virus (HVT), a strain of chicken herpes virus, or a combination thereof and/or a strain of Newcastle disease virus in the vaccine diluent;
    suspending the concentrated strain of *Lactobacillus* probiotic bacteria in the vaccine diluent; and
    administering the *Lactobacillus* probiotic bacteria and the strain of turkey herpes virus (HVT), the strain of chicken herpes virus, or the combination thereof and/or the strain of Newcastle disease virus in the vaccine diluent to an embryonic poultry egg.

2. The method of claim 1, wherein said administering results in reduced levels of enterobacterial pathogens in the poultry, colonization of the poultry with said probiotic bacteria, increased poultry hatchability or reduced poultry mortality.

3. The method of claim 1, wherein said strain of *Lactobacillus* probiotic bacteria is *Lactobacillus reuteri* strain T-1 (ATCC 55149) or *Lactobacillus reuteri* strain 11284 (ATCC 55148), or a combination thereof.

4. The method of claim 1, wherein said turkey herpes virus (HVT) is the FC-128 strain and/or said chicken herpes virus is the SB-1 strain.

5. The method of claim 1, wherein said Newcastle disease virus is one of more than one of the C4, V4-HR, I-2, F, B-1 or La Sota strain of Newcastle disease virus.

6. The method of claim 1, wherein said vaccine diluent has a pH of 6.9 to 7.3.

7. The method of claim 1, wherein the vaccine diluent comprises sucrose in a concentration of about 2% to about 10% weight per volume (w/v); N.Z. Amine AS in a concentration of about 0.25% to about 2.75% (w/v); dibasic potassium phosphate in a concentration of about 0.06% to about 0.20%; and monobasic potassium phosphate in a concentration of about 0.02% to about 0.07% (w/v).

* * * * *